(12) United States Patent
Van Kruchten et al.

(10) Patent No.: US 7,488,835 B2
(45) Date of Patent: Feb. 10, 2009

(54) PROCESS FOR THE PREPARATION OF ALKYLENE CARBONATES

(75) Inventors: Eugene Marie Godfried Andre Van Kruchten, Amsterdam (NL); Hendrik Stichter, Amsterdam (NL); Johannes Theodorus Gertruda Wijenberg, Amsterdam (NL)

(73) Assignee: Shell Oil Company, Houston, TX (US)

( * ) Notice: Subject to any disclaimer, the term of this patent is extended or adjusted under 35 U.S.C. 154(b) by 23 days.

(21) Appl. No.: 11/461,325

(22) Filed: Jul. 31, 2006

(65) Prior Publication Data

US 2007/0179303 A1 Aug. 2, 2007

(30) Foreign Application Priority Data

Aug. 2, 2005 (EP) ................... 05254835

(51) Int. Cl.
*C07D 317/36* (2006.01)
*C07D 317/38* (2006.01)

(52) U.S. Cl. .................................... 549/230
(58) Field of Classification Search .................. 549/230
See application file for complete search history.

(56) References Cited

U.S. PATENT DOCUMENTS

| | | | | |
|---|---|---|---|---|
| 4,160,116 A | 7/1979 | Mieno et al. | ................. | 568/867 |
| 4,283,580 A | 8/1981 | Odanaka et al. | ............. | 568/858 |
| 4,307,256 A | 12/1981 | Cipriani et al. | ............. | 568/867 |
| 4,314,945 A | 2/1982 | McMullen et al. | ........ | 260/340.2 |
| 4,786,741 A | 11/1988 | Sachs | .......................... | 549/230 |
| 4,982,021 A | 1/1991 | Best et al. | .................... | 568/867 |
| 5,138,073 A | 8/1992 | Harvey | ........................ | 549/230 |
| 5,488,184 A | 1/1996 | Reman et al. | ................ | 568/867 |
| 6,080,897 A | 6/2000 | Kawabe | ........................ | 568/858 |
| 6,124,508 A | 9/2000 | Van Kruchten | .............. | 568/867 |
| 6,153,801 A | 11/2000 | Van Kruchten | .............. | 568/867 |
| 6,187,972 B1 * | 2/2001 | Kawabe et al. | .............. | 568/858 |
| 2005/0014980 A1 | 1/2005 | Van Hal et al. | .............. | 568/867 |
| 2007/0191648 A1 | 8/2007 | Van Kruchten et al. | ..... | 568/867 |

FOREIGN PATENT DOCUMENTS

| | | |
|---|---|---|
| EP | 156449 | 3/1985 |
| EP | 1034158 | 9/2000 |
| JP | 56-092228 | 7/1981 |
| JP | 56092228 | 7/1981 |
| JP | 56-128778 | 10/1981 |
| JP | 57-106631 | 7/1982 |
| JP | 59-013741 | 1/1984 |
| JP | 2001/151711 | 6/2001 |
| JP | 2001/151713 | 6/2001 |

OTHER PUBLICATIONS

Kasuga, K. et al, "The fixation of carbon dioxide with 1,2-expoxypropane catalyzed by alkali-metal halide in the presence of a crown ether", Inorganica Chimica ACTA, vol. 257, 1997, pp. 277-278.
Aldrich: Handbook of Fine Chemicals and Laboratory Equipment, 15-Crown 5 entry and Material Data Safety Shett, Aldrich Catalougue, Handbook of Fine Chemicals, 2006.
Rokicki et al, "Cyclic Carbonates Obtained by Reactions of Metal Carbonates with Ephihalohydrins", Bulletin of the Chemical Society, Japan, Tokyo, vol. 57, No. 6, 1984, pp. 1662-1666.
Abbas-Alli G. et al, "Organic Carbonates", Chem. Rev. 1996, pp. 951-976.
Notice of Allowance for U.S. Appl. No. 11/461,334 dated Mar. 28, 2008.

* cited by examiner

*Primary Examiner*—Bernard Dentz

(57) ABSTRACT

A process for the catalytic carboxylation of alkylene oxides with carbon dioxide, in the presence of a catalyst composition and water, wherein the catalyst composition comprises an alkali metal halide and a macrocyclic chelating compound.

17 Claims, No Drawings

PROCESS FOR THE PREPARATION OF ALKYLENE CARBONATES

This application claims the benefit of EPC 05254835.1.

FIELD OF THE INVENTION

The invention relates to a process for the preparation of alkylene carbonates by the catalytic carboxylation of alkylene oxides.

BACKGROUND OF THE INVENTION

Alkylene carbonates, such as ethylene carbonate and propylene carbonate are widely used as solvents and diluents in industrial processes. They are regularly used as raw materials for commercial products such as cosmetics and pharmaceuticals. Alkylene carbonates can also be used as intermediates in the preparation of alkylene glycols from alkylene oxides.

Alkylene carbonates are produced commercially by the reaction of carbon dioxide with the appropriate alkylene oxide. In the art, ionic halides, such as quaternary ammonium halides, quaternary phosphonium halides and metal halides, are frequently proposed as catalysts for this reaction.

According to JP-A-57,106,631, the preparation of alkylene carbonate as an intermediate in the two-step preparation of alkylene glycol can occur by the reaction of an alkylene oxide with carbon dioxide in the presence of an alkali metal halide.

U.S. Pat. No. 4,314,945 is directed to the preparation of an alkylene carbonate by reaction of the corresponding alkylene oxide with carbon dioxide in the presence of a catalyst characterized by the formula $M^+A^-$, wherein M is potassium and A is iodine or M is a quaternary ammonium cation $(R_1R_2R_3R_4N^+)$ and A is either bromine, chlorine or iodine. The reaction is carried out in alkylene carbonate.

U.S. Pat. No. 4,786,741 is directed to the reaction of alkylene oxides with carbon dioxide in the presence of a catalytic composition and water. Catalytic compositions listed include organic quaternary ammonium halides, organic quaternary phosphonium halides, organic sulphonium halides and organic antimony halides.

JP-A-59,013,741 teaches a method for producing ethylene glycol from ethylene oxide via ethylene carbonate. The reaction of ethylene oxide with carbon dioxide to form ethylene carbonate is catalysed with a quaternary phosphonium halide.

Quaternary phosphonium and ammonium halides are known to degrade under reaction conditions suitable for the carboxylation of alkylene oxides. This can lead to contamination of the product stream with degradation products and hence a reduction in the purity of the required product. In the case of quaternary ammonium halides the degradation products can include amines, which are stench compounds and may be detected by their odour at very low levels of contamination (e.g. ppm or ppb levels).

There are several examples in the prior art of the combination of metal halides with polyethers such as polyethylene glycol and crown ethers as a catalytic composition for the carboxylation reaction of alkylene oxides to alkylene carbonates.

The fixation of atmospheric carbon dioxide, as propane-1,2-diol carbonate, by reaction with 1,2-epoxypropane is taught in K. Kasuga, N. Kabata, Inorganica Chimica Acta, 257 (1997) 277. Here, a combination of sodium iodide and 15-crown-5 was found to give the highest yield of propane-1,2-diol carbonate for this reaction, when carried out in either chloroform or dichloromethane.

The experiments described in G. Rokicki, W. Kuran, B. Pogozelska-Marciniak Monatshefte für Chemie, 115 (1984) 205 are directed to the use of potassium salt-phase transfer agent systems as catalysts in the reactions of a variety of epoxides with carbon dioxide to yield the corresponding carbonates. In these experiments, the reaction is carried out in the absence of a solvent.

In W. Huang, S. Wu, et al. Fenzi Cuihua, 12 (1998) 447-452, the use of cycloethers containing metallic iron is compared with the use of di-, tri- and polyethylene glycols and dibenzo-18-crown-6 as carboxylation catalysts in combination with potassium iodide for the reaction of ethylene oxide with carbon dioxide in tetrahydrofuran, which has been dried prior to use.

JP-A-56,128,778 is directed to the combination of alkali metal halides with crown compounds in the preparation of alkylene carbonates. The preparation reaction is again carried out in the absence of a solvent.

The explosion potential of epoxides is well known. Therefore, the use of such compounds undiluted would be unfavourable on a commercial scale.

SUMMARY OF THE INVENTION

The present invention provides a process for the catalytic carboxylation of alkylene oxides with carbon dioxide, in the presence of a catalytic composition and water, wherein the catalyst composition comprises an alkali metal halide and a macrocyclic chelating compound.

DETAILED DESCRIPTION OF THE INVENTION

We have now surprisingly found that a catalytic composition comprising an alkali metal halide and a macrocyclic chelating compound catalyses the carboxylation of alkylene oxides to the corresponding alkylene carbonates, in the presence of carbon dioxide and water, with an increased activity and rate of reaction compared to the catalytic carboxylation of an alkylene oxide to the corresponding alkylene carbonate using the catalytic compositions and conditions taught in the prior art.

Furthermore, in this process the use and subsequent separation and disposal of organic solvents is unnecessary while the explosion risk due to undiluted alkylene oxide is also diminished.

The alkylene oxides used as starting material in the process of the invention have their conventional definition, i.e. they are compounds having a vicinal oxide (epoxy) group in their molecules.

Particularly suitable are alkylene oxides of the general formula (I),

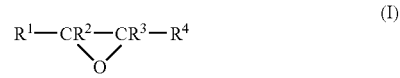

(I)

wherein $R^1$ to $R^4$ independently represent a hydrogen atom or an optionally substituted, alkyl group having from 1 to 6 carbon atoms. Any alkyl group, represented by $R^1$, $R^2$, $R^3$ and/or $R^4$ preferably has from 1 to 3 carbon atoms. As substituents, inactive moieties, such as hydroxy groups may be present. Preferably, $R^1$, $R^2$ and $R^3$ represent hydrogen atoms and $R^4$ represents a non-substituted $C_1$-$C_3$-alkyl group and, more preferably, $R^1$, $R^2$, $R^3$ and $R^4$ all represent hydrogen atoms.

Examples of suitable alkylene oxides therefore include ethylene oxide, propylene oxide, 1,2-epoxybutane and 2,3-epoxybutane. In the present invention the most preferred alkylene oxide is ethylene oxide.

The preparation of alkylene oxides is well known to the skilled person. In the case of ethylene oxide, it may be prepared by the well known direct oxidation of ethylene, i.e. by air or oxygen oxidation, utilizing silver-based catalysts and often also organic moderators, e.g. organic halides (see for example Kirk Othmer's Encyclopedia of Chemical Technology, 4th edition, Vol. 9, pages 923-940).

As used herein, the term alkylene carbonate refers to five-membered alkylene carbonates (1,3-dioxolan-2-ones) of the general formula (II),

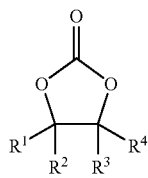

(II)

wherein $R^1$ to $R^4$ correspond to $R^1$ to $R^4$ of the parent alkylene oxide. Therefore suitable alkylene carbonates include ethylene carbonate, propylene carbonate, 1,2-butylene carbonate and 2,3-butylene carbonate. In the present invention the most preferred alkylene carbonate of the general formula (II) is ethylene carbonate, where $R^1$, $R^2$, $R^3$ and $R^4$ all represent hydrogen atoms.

As used herein, alkali metal halide refers to a halide of a metal selected from group 1 of the periodic table (according to IUPAC Nomenclature of Inorganic Chemistry, Recommendations 1990. Blackwell Scientific Publications, 1990. Edited by G J Leigh). Preferably the group 1 metal is selected from sodium, potassium, lithium and cesium. Most preferably, the group 1 metal is potassium. Suitably, the halide is selected from iodide, chloride and bromide. Most suitably, the halide is an iodide.

Macrocyclic chelating compounds are known—see for example J. March in Advanced Organic Chemistry; Reactions, Mechanisms and Structures, 4th Edition 1992, pp 82-87 and 363-364. They have the property of forming complexes with positive ions (cations), although they can also form complexes with neutral molecules. They have a regular organic ring structure containing a plurality of heteroatoms such as oxygen, nitrogen or sulphur. They can be monocyclic, bicyclic or cycles of a higher order. The bonding of cations in these complexes is the result of ion-dipole attractions between the heteroatoms and the positive ions. Thus, the number of the heteroatoms in the molecule determines the binding strength and the size and shape of the cavity determines the ions (or neutral molecules) that can be bound. The macrocycle is called the host and the ion is the guest. Owing to their shape and size, the ability of the host molecules to bind guests is often very specific, enabling the host to pull just one cation or molecule out of a mixture.

It is envisaged that any macrocyclic chelating compound may be utilized in the process of the present invention.

The best-known macrocyclic chelating compounds are those wherein all or most of the heteroatoms are oxygen, in particular the crown ethers wherein the ring structure is two-dimensional (monocyclic) and the cryptands wherein the ring structure is three-dimensional (bicyclic, tricyclic etc.). When the cavity of the macrocycle is spherical the molecule is called spherand. Other more exotic types are the calixarenes, cryptophanes, hemispherands and pondands.

Crown ethers are usually denoted by their total number of atoms and number of heteroatoms in the ring, plus substituents when present. Examples are 12-crown-4 (III), 15-crown-5 (IV) and dicyclohexano-18-crown-6 (V).

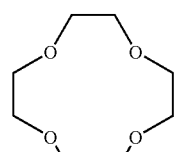

(III)

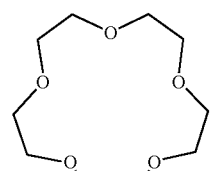

(IV)

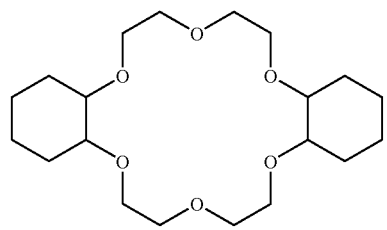

(V)

In the present invention, the macrocyclic chelating compound is preferably selected from the group of crown ethers and cryptands. More preferably, the macrocyclic chelating compound is a crown ether, selected from 18-crown-6, dibenzo-18-crown-6, 15-crown-5, 12-crown-4, benzo-15-crown-5 or 21-crown-7. Even more preferably, the crown ether is 18-crown-6 or dibenzo-18-crown-6.

The macrocyclic chelating compound and halide may be mixed to form a complex before addition to the reaction mixture, or the macrocyclic chelating compound and the iodide may be added to the reaction mixture separately.

Preferably, the total amount of carbon dioxide supplied to the reactor is an amount of at least 0.5 mol/mol alkylene oxide, preferably at least 1 mol/mol alkylene oxide. Preferably the total amount of carbon dioxide supplied to the reactor is an amount of at most 100 mol/mol alkylene oxide, more preferably in an amount of at most 10 mol/mol alkylene oxide.

As used herein, the reaction being carried out in the presence of water refers to the reaction being carried out in an amount of water sufficient to enable an increase in the reaction rate and the catalyst activity in the reaction over the same reaction carried out in the substantial absence of water. The amount of water present is usually at least 0.05 mol/mol alkylene oxide present in the reaction mixture, preferably at least 0.1 mol/mol alkylene oxide. An amount of water present of at least 0.2 mol/mol alkylene oxide is most preferred. Preferably, the amount of water present is less than 10 mol/mol alkylene oxide, more preferably less than 5 mol/mol of alkylene oxide. An amount of water present of at most 2 mol/mol alkylene oxide is most preferred. Very good results have been obtained using an amount of water in the range of from 0.5 to 2 mol/mol alkylene oxide.

It is a further benefit of the present invention that a close to stoichiometric amount of water to alkylene oxide, for example an amount of water in the range of from 1 mol/mol alkylene oxide to 1.3 mol/mol alkylene oxide, is particularly suitable for the process of the present invention. The use of this amount of water not only provides excellent activity and reaction rate, but it also reduces the amount of energy required for the removal of excess water, if necessary, from the reaction product. Alternatively, if the product alkylene carbonate is subsequently to be converted into the corresponding alkylene glycol, a suitable amount of water is already present in the reaction mixture.

The water present in the reaction mixture of the present invention may be added to the reaction mixture separately from the alkylene oxide. Alternatively the alkylene oxide and water may be pre-mixed before being supplied to the reactor. In a preferred embodiment of the invention, an alkylene oxide product mixture from an alkylene oxide reactor is used either without further process steps or after some concentration in a stripper. Most preferably, an ethylene oxide/water mixture, formed by absorption with water of the product stream from a direct oxidation ethylene oxide reactor is used. This method has a further benefit that the energy expended in isolating the alkylene oxide, prior to the process of the invention, is reduced.

Suitably, the molar ratio of macrocyclic chelating compound to halide in the reaction mixture is at least 0.25:1, more suitably the molar ration of macrocyclic chelating compound to halide is at least 0.5:1, most suitably the molar ratio of macrocyclic chelating compound to halide is at least 0.75:1. Suitably, the molar ratio of macrocyclic chelating compound to halide is at most 10:1, more suitably the molar ratio of macrocyclic chelating compound to halide is at most 5:1.

Suitably, the halide is present in amount in the range of from 0.0001 to 0.5 mol/mol alkylene oxide. Preferably, the halide is present in an amount in the range of from 0.001 to 0.1 mol/mol alkylene oxide.

The process of the present invention can be carried out in any reaction system suitable for a carboxylation process. In particular, a reaction system comprising at least one bubble column is suitable.

The process of the present invention may be carried out in batch operation. However, in particular for large-scale embodiments, it is preferred to operate the process continuously.

Suitable reaction temperatures for the catalytic carboxylation of alkylene oxides, according to the present invention are generally in the range of from 40 to 200° C.; temperatures in the range of from 50 to 120° C. are preferred.

The reaction pressure is usually selected in the range of from 100 to 5000 kPa, preferably in the range of from 200 to 3000 kPa, most preferably in the range of from 500 to 2000 kPa.

The following Examples will illustrate the invention. Examples 1 to 6 are comparative and Examples 7 to 22 are of the invention.

EXAMPLES

The Examples were carried out in either a 250 or a 125 ml Medimex autoclave according to the following procedures.

General Reaction Conditions

Examples 1 to 5, 7 to 9 and 13 to 22

The reactor was filled with water and the alkali metal halide catalyst and, for Examples 5, 7 to 9 and 13 to 22, crown ether or PEG were added in the required ratio to provide a concentration of halide ions of 0.12 mol/l. The reactor was then purged with $CO_2$ and pressurised with a $CO_2$ atmosphere of approximately 5 bar (500 kPa). The reactor content was then heated to 80° C. and the reactor was further pressurised to 20 bar (2,000 kPa). The ethylene oxide was then pumped into the reactor at a rate of 6.3 g/min until a water/EO ratio of 1.8 mol/mol was reached for Examples 1 to 5, 7 to 9, 13 and 15 to 22, or the specific water/EO ratio was reached (see Table 3) in the case of Examples 10, 11, 12 and 14. These conditions result in a halide concentration of 0.0118 mol/mol ethylene oxide. The reactor content was maintained at the above temperature and pressure (by the continuous supply of $CO_2$) and samples were taken at regular time intervals and analysed by gas liquid chromatography (GLC).

Reaction Conditions

Example 6 and 10 to 12

The reactor was filled with propylene carbonate (Example 6) or a propylene carbonate/water mixture in the amounts detailed in Table 3 (Examples 10 to 12), and the alkali metal halide catalyst and crown ether were added in the required ratio to provide a concentration of halide ions of 0.12 mol/l. The reactor was then purged with $CO_2$ and pressurised with a $CO_2$ atmosphere of approximately 5 bar (500 kPa). The reactor content was then heated to 80° C. and the reactor was further pressurised to 20 bar (2,000 kPa). The ethylene oxide was then pumped into the reactor at a rate of 6.3 g/min until the same concentration was achieved as in the General Reaction Conditions. These conditions result in a $CO_2$ intake of 1.3 moles per mole of ethylene oxide and a halide concentration of 0.0118 mol/mol ethylene oxide. The reactor content was maintained at the above temperature and pressure (by the continuous supply of $CO_2$) and samples were taken at regular time intervals and analysed by GLC.

Following the above procedures, a wide range of catalyst compositions were tested (Examples 1 to 7 and 15 to 22). Variation of the ratio of crown ether to iodide (Examples 7 to 9) and of the ratio of water to ethylene oxide (Examples 10 to 14) were separately investigated following the same general experimental procedures, adjusted as necessary. The results are shown in Tables 1 to 4.

TABLE 1

Comparative Examples (1 to 6) and Example of the invention (7)

| EG No. | Catalyst | Ether | Crown ether:iodide ratio (mol/mol) | EO conversion (% mol) 60 min | EC selectivity (% mol) | TOF[#] |
|---|---|---|---|---|---|---|
| 1 | KI | — | — | 62 | 90 | 47 |
| 2 | NaI | — | — | 59 | 92 | 45 |
| 3 | LiI | — | — | 35 | 90 | 26 |
| 4 | CsI | — | — | 65 | 92 | 50 |
| 5 | KI | PEG-400 | 1 | 64 | 92 | 50 |
| 6* | KI | 18-crown-6 | 1 | 15 | 99 | 13 |
| 7 | KI | 18-crown-6 | 1 | 75 | 93 | 60 |

*no water; solvent used = propylene carbonate. PEG = polyethylene glycol.
[#]TOF = Turn over frequency (moles of EC produced/mole of iodide catalyst/h)

TABLE 2

Ratio of crown ether to iodide

| EG No. | Catalyst | Ether | Crown ether:iodide ratio (mol/mol) | EO conversion (% mol) 60 min | EC selectivity (% mol) | TOF[#] |
|---|---|---|---|---|---|---|
| 8 | KI | 18-crown-6 | 0.33 | 69 | 94 | 55 |
| 7 | KI | 18-crown-6 | 1 | 75 | 93 | 60 |
| 9 | KI | 18-crown-6 | 2 | 76 | 94 | 60 |

[#]TOF = Turn over frequency (moles of EC produced/mole of iodide catalyst/h)

TABLE 3

Ratio of water to ethylene oxide (all carried out with a crown ether:iodide ratio of 1 mol/mol)

| EG No. | Catalyst | Crown ether | Water:ethylene oxide ratio (mol/mol) | Water (ml) | Propylene carbonate (ml) | EO conversion (% mol) 60 min | EC selectivity (% mol) | TOF[#] |
|---|---|---|---|---|---|---|---|---|
| 6* | KI | 18-crown-6 | 0 | — | 25 | 15 | 99 | 13 |
| 10 | KI | 18-crown-6 | 0.20 | 3 | 23 | 60 | 99 | 51 |
| 11 | KI | 18-crown-6 | 0.50 | 7 | 29 | 81 | 99 | 69 |
| 12 | KI | 18-crown-6 | 1.02 | 14 | 11 | 84 | 98 | 72 |
| 13 | KI | 18-crown-6 | 1.80 | 25 | — | 75 | 95 | 62 |
| 14 | KI | 18-crown-6 | 4.01 | 34 | — | 57 | 83 | 28 |

[#]TOF = Turn over frequency (moles of EC produced/mole of iodide catalyst/h)

TABLE 4

Further examples

| EG No. | Catalyst | Crown ether | Crown ether:iodide ratio (mol/mol) | EO conversion (% mol) 60 min | EC selectivity (% mol) | TOF[#] |
|---|---|---|---|---|---|---|
| 15 | KI | Dibenzo-18-crown-6 | 1 | 77 | 93 | 61 |
| 16 | NaI | 15-crown-5 | 1 | 69 | 93 | 54 |
| 17 | NaI | Benzo-15-crown-5 | 1 | 67 | 93 | 52 |
| 18 | NaI | 18-crown-6 | 1 | 72 | 91 | 55 |
| 19 | LiI | 12-crown-4 | 1 | 51 | 90 | 38 |
| 20 | CsI | 18-crown-6 | 1 | 73 | 91 | 55 |
| 21 | CsI | 21-crown-7 | 1 | 72 | 95 | 58 |
| 22 | KBr | 18-crown-6 | 1 | 43 | 90 | 33 |

[#]TOF = Turn over frequency (moles of EC produced/mole of iodide catalyst/h)

The results in Table 1 demonstrate an increase in activity of the catalyst (shown by an increase in EO conversion) and an increase in reaction rate (shown by an increase in TOF) for the process of the invention (Example 7) over processes involving catalyst compositions comprising either a linear chelating compound (Example 5) or no chelating compound (Examples 1 to 4). These advantages are also shown for the process of the present invention over the same process carried out in the absence of water (Example 6).

A range of ratios of crown ether:iodide can successfully be used in the process of the invention as shown in Table 2.

The use of water in the reaction mixture leads to a large improvement in yield and activity as shown by the Examples in Table 3. Further, the invention can be successfully applied to reaction mixtures comprising a wide range of water:ethylene oxide ratios.

A wide range of catalytic compositions can be used within the scope of the present invention (Examples 15 to 22).

The invention claimed is:

1. A process for the catalytic carboxylation of alkylene oxides with carbon dioxide, in the presence of a catalyst composition and water, wherein the catalyst composition comprises an alkali metal halide and a macrocyclic chelating compound, and wherein the water is present in an amount of at least 0.05 moles per mole of alkylene oxide.

2. A process as claimed in claim 1, wherein the halide is an iodide and the alkali metal is selected from the group consisting of sodium, potassium, lithium and cesium.

3. A process as claimed in claim 2, wherein the alkali metal halide is potassium iodide.

4. A process as claimed in claim 1, wherein the macrocyclic chelating compound is a crown ether selected from the group consisting of 18-crown-6, dibenzo-18-crown-6,15-crown-5, 12-crown-4, benzo-15-crown-5 or 21-crown-7.

5. A process as claimed in claim 1, wherein the catalyst composition is potassium iodide combined with 18-crown-6 or dibenzo-18-crown-6.

6. A process as claimed in claim 1, wherein the molar ratio of macrocyclic chelating compound to halide is in the range of from 0.25:1 to 10:1.

7. A process as claimed in claim 6, wherein the molar ratio of macrocyclic chelating compound to halide is in the range of from 0.75:1 to 5:1.

8. A process as claimed in claim 1, wherein the process takes place at a temperature in the range of from 40 to 200° C. and at a pressure in the range of from 100 to 5000 kPa.

9. A process as claimed in claim 1, wherein the water is present in an amount in the range of from 0.05 to 10 moles per mole of alkylene oxide present in the reaction mixture.

10. A process as claimed in claim 1, wherein the alkylene oxide is ethylene oxide.

11. A process for the catalytic carboxylation of alkylene oxides with carbon dioxide, in the presence of a catalyst composition and water, wherein the catalyst composition comprises potassium iodide and a macrocyclic chelating compound, and wherein the water is present in an amount of at least 0.05 moles per mole of alkylene oxide.

12. A process as claimed in claim 11, wherein the macrocyclic chelating compound is a crown ether selected from the group consisting of 18-crown-6, dibenzo-18-crown-6,15-crown-5,12-crown-4, benzo-15-crown-5 or 21-crown-7.

13. A process as claimed in claim 11, wherein the molar ratio of macrocyclic chelating compound to potassium iodide is in the range of from 0.25:1 to 10:1.

14. A process as claimed in claim 11, wherein the molar ratio of macrocyclic chelating compound to potassium iodide is in the range of from 0.75:1 to 5:1.

15. A process as claimed in claim 11, wherein the process takes place at a temperature in the range of from 40 to 200° C. and at a pressure in the range of from 100 to 5000 kPa.

16. A process as claimed in claim 11, wherein the water is present in an amount in the range of from 0.05 to 10 moles per mole of alkylene oxide present in the reaction mixture.

17. A process for the catalytic carboxylation of alkylene oxides with carbon dioxide, in the presence of a catalyst composition and water, wherein the catalyst composition comprises potassium iodide and a macrocyclic chelating compound that is a crown ether selected from the group consisting of 18-crown-6, dibenzo-18-crown-6, 15-crown-5, 12-crown-4, benzo-15-crown-5 or 21-crown-7, and wherein the water is present in an amount of at least 0.05 moles per mole of alkylene oxide.

\* \* \* \* \*